US008586014B2

(12) United States Patent
Masse et al.

(10) Patent No.: US 8,586,014 B2
(45) Date of Patent: Nov. 19, 2013

(54) COMPOSITION FOR THE CARE OF KERATIN MATERIAL AND COSMETIC TREATMENT PROCESS USING SAID COMPOSITION

(75) Inventors: Virginie Masse, Clichy (FR); Sandrine Decoster, Saint-Gratien (FR)

(73) Assignee: L'Oreal, Paris (FR)

( * ) Notice: Subject to any disclaimer, the term of this patent is extended or adjusted under 35 U.S.C. 154(b) by 1117 days.

(21) Appl. No.: 11/589,070

(22) Filed: Oct. 30, 2006

(65) Prior Publication Data

US 2007/0104668 A1 May 10, 2007

Related U.S. Application Data

(60) Provisional application No. 60/736,298, filed on Nov. 15, 2005.

(30) Foreign Application Priority Data

Oct. 28, 2005 (FR) ...................................... 05 11097

(51) Int. Cl.
*A61K 8/89* (2006.01)
*A61K 8/02* (2006.01)
*A61Q 5/00* (2006.01)
*A61Q 5/02* (2006.01)
*A61Q 5/12* (2006.01)

(52) U.S. Cl.
USPC ..................... 424/70.12; 424/401; 424/70.31; 424/70.1

(58) Field of Classification Search
USPC ............................ 424/70.12, 401, 70.31, 70.1
See application file for complete search history.

(56) References Cited

U.S. PATENT DOCUMENTS

| | | |
|---|---|---|
| 2,261,002 A | 6/1939 | Bergmann |
| 2,271,378 A | 1/1942 | Searle et al. |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,578 A | 6/1971 | Kamphausen |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,579,732 A | 4/1986 | Grollier et al. |
| 4,591,610 A | 5/1986 | Grollier |

(Continued)

FOREIGN PATENT DOCUMENTS

| | | |
|---|---|---|
| CA | 1 201 952 | 3/1986 |
| EP | 0 080 976 A1 | 6/1983 |

(Continued)

OTHER PUBLICATIONS

Cosmetics and Toiletries, vol. 91, Jan. 1976, p. 29-32—Todd & Byers "Volatile silicone fluids for cosmetic formulations".

(Continued)

*Primary Examiner* — Rachael E Bredefeld
(74) *Attorney, Agent, or Firm* — O'Brien Jones, PLLC

(57) ABSTRACT

The present disclosure relates to a cosmetic composition for the care of keratin materials and which comprises, in an aqueous medium:
at least one silicone,
at least one mono- or diester of a fatty acid and of ethylene glycol or of polyethylene glycol, and
at least one ester of a $C_8$ to $C_{14}$ fatty acid and of an oxyethylenated sorbitan comprising from 2 to 10 oxyethylene units. The present disclosure also relates to a process for the cosmetic treatment of keratin materials using the composition.

27 Claims, No Drawings

(56) References Cited

U.S. PATENT DOCUMENTS

| | | | |
|---|---|---|---|
| 4,608,250 | A | 8/1986 | Jacquet et al. |
| 4,719,099 | A | 1/1988 | Grollier et al. |
| 4,761,273 | A | 8/1988 | Grollier et al. |
| 4,777,040 | A | 10/1988 | Grollier et al. |
| 4,803,221 | A | 2/1989 | Bair |
| 4,839,166 | A | 6/1989 | Grollier et al. |
| 4,948,579 | A | 8/1990 | Jacquet et al. |
| 4,957,732 | A | 9/1990 | Grollier et al. |
| 4,970,066 | A | 11/1990 | Grollier et al. |
| 4,978,561 | A | 12/1990 | Cray et al. |
| 4,996,059 | A | 2/1991 | Grollier et al. |
| 5,009,880 | A | 4/1991 | Grollier et al. |
| 5,057,311 | A | 10/1991 | Kamegai et al. |
| 5,089,252 | A | 2/1992 | Grollier et al. |
| 5,139,037 | A | 8/1992 | Grollier et al. |
| 5,196,189 | A | 3/1993 | Jacquet et al. |
| 5,958,392 | A | 9/1999 | Grollier et al. |
| 6,475,499 | B2 * | 11/2002 | Maubru et al. ................ 424/401 |
| 2004/0180030 | A1 * | 9/2004 | Maubru ..................... 424/70.21 |
| 2004/0185020 | A1 | 9/2004 | Gawtrey et al. |
| 2004/0197287 | A1 * | 10/2004 | Kaczvinsky et al. ...... 424/70.13 |

FOREIGN PATENT DOCUMENTS

| | | |
|---|---|---|
| EP | 0 122 324 A1 | 10/1984 |
| EP | 0 337 354 A1 | 10/1989 |
| EP | 0 342 834 B1 | 11/1989 |
| FR | 1 492 597 | 9/1966 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2589476 | 5/1987 |
| FR | 2 598 611 | 11/1987 |
| FR | 2 804 020 | 7/2001 |
| FR | 2 848 829 | 6/2004 |
| WO | WO 97/33561 | 9/1997 |

OTHER PUBLICATIONS

"Handbook of Surfactants" by M.R. Porter, publisher Blackie & Son (Glasgow and London), 1991, pp. 116-178.
Walter Noll, "Chemistry and Technology of Silicones" (Academic Press 1968).
English language freepatentsonline abstract of EP 0 080 976.
English language esp@cenet abstract of EP 0 122 324.
English language Derwent abstract of FR 2 336 434.
English language esp@cenet abstract of FR 2 589 476.

* cited by examiner

COMPOSITION FOR THE CARE OF KERATIN MATERIAL AND COSMETIC TREATMENT PROCESS USING SAID COMPOSITION

This application claims benefit of U.S. Provisional Application No. 60/736,298 filed Nov. 15, 2005, the contents of which are incorporated herein by reference. This application also claims benefit of priority under 35 U.S.C. §119 to French Patent Application No. FR 05 11097, filed Oct. 28, 2005, the contents of which are also incorporated herein by reference.

The present disclosure relates to an improved cosmetic composition for the care of keratin materials, such as the washing and/or the cosmetic treatment of the hair and/or of the skin, and which comprises at least one silicone, at least one mono- or diester of a fatty acid and of ethylene glycol or of polyethylene glycol, and also at least one ester of a $C_8$ to $C_{14}$ fatty acid and of an oxyethylenated sorbitan comprising from 2 to 10 oxyethylene units.

The present disclosure also relates to a cosmetic treatment process using the composition.

Numerous compositions for washing keratin materials have been described in the prior art.

For example, French Patent Application FR 2 848 829 describes detergent compositions intended, for instance, for washing the hair, which exhibit improved cosmetic properties, in particular in terms of untangling, smoothing, suppleness, malleability and/or softness of the hair.

These compositions comprise at least one alkylamphohydroxyalkyl sulphonate amphoteric surfactant, and at least one silicone chosen from non-organomodified silicones having a viscosity ranging from 500 mm$^2$/s to 1 000 000 mm$^2$/s and organomodified silicones.

Canadian Patent CA 1 201 952 describes surfactant compositions intended for the formulation of cosmetic compositions, in particular of shampoos, the foaming capacity of which is improved. These compositions comprise
  from 3.75 to 15% by weight of an anionic surfactant such as a lauryl ether sulphate,
  from 1 to 4.20% by weight of an amphoteric surfactant such as an alkylamidobetaine,
  from 0.7 to 3% by weight of a nonionic surfactant such as a polyoxyethylenated sorbitan, and
  from 0.1 to 4% by weight of a "soap" chosen from fatty acids, alkyl isethionates, alkyl taurides and alkyl sarcosides.

Published U.S. Patent Application US 2004/0197287 describes anti-dandruff shampoos, the detergent and/or anti-dandruff properties of which are improved. These compositions comprise:
  from 5 to 50% by weight of a detergent surfactant,
  from 0.1 to 4% by weight of an anti-dandruff agent,
  from 0.1 to 50% by weight of an ester of a fatty acid and of a polyoxyethylenated sorbitan, such as at least one of the products sold under the names TWEEN 40, TWEEN 60, TWEEN 61 and TWEEN 85 by the company Uniqema, and
  at least 20% by weight of water.

Finally, International Patent Application WO 97/33561 describes cleansing compositions for the hair and the skin, which may exhibit a low degree of eye irritation. These compositions comprise:
  from 5 to 20% by weight of a mixture of surfactants, including one nonionic surfactant, one amphoteric surfactant and one anionic surfactant, and
  from 0.01 to 3% by weight of a humectant, such as a cationic polyol.

As nonionic surfactant, use is made, inter alia, of polyoxyethylenated derivatives of an ester of a fatty acid and of a polyol, containing from 10 to 120 oxyethylene units.

However, the compositions described in the prior art may have certain deficiencies. In particular, the most effective shampoos can cause stinging in the eyes when the diluted product runs into the eye, which frequently occurs in children. Moreover, a large number of these shampoos can cause reactions of discomfort such as redness, itching or stinging in individuals with sensitive skin.

The gentle compositions proposed in the prior art may exhibit, on the other hand, insufficient qualities for use (inadequate viscosities, mediocre initiation and/or quality of foam) and cosmetic properties which may also be insufficient, in particular in terms of softness and, for the hair, also in terms of untangling and smoothing.

The present inventors have now discovered, surprisingly, that by combining, in the presence of a silicone, a specific pearlescent agent and a specific surfactant, it is possible to formulate cosmetic compositions which may be particularly gentle and non-aggressive, and may have good qualities for use, in particular in terms of viscosity, and which at the same time may exhibit both detergent and cosmetic properties that are excellent.

Thus, the compositions according to the present disclosure make it possible to decrease the reactions of discomfort on the skin and the scalp, and to have an excellent degree of ocular tolerance. In parallel, they may have cleansing properties which are of a good level and also excellent cosmetic properties, such as a good degree of softness and, as regards the hair, besides this good degree of softness, may also have good untangling and smoothing. In addition, they may have an aesthetic pearlescent appearance.

A subject of the present disclosure is therefore a cosmetic composition for the care of keratin materials, comprising, in an aqueous medium:
  at least one silicone,
  at least one mono- or diester of a fatty acid and of ethylene glycol or of polyethylene glycol, and
  at least one ester of a $C_8$ to $C_{14}$ fatty acid and of an oxyethylenated sorbitan comprising from 2 to 10 oxyethylene units.

Another subject of the present disclosure is a cosmetic treatment process using the composition.

Other subjects and characteristics, aspects and advantages of the present disclosure will emerge even more clearly on reading the description and the examples which follow.

In the present disclosure, and in a manner known per se, the expression "compound with X OE" denotes an oxyethylenated compound comprising X units of oxyethylene per molecule.

In addition, the term "CY compound," as used herein, denotes a compound comprising Y carbon atoms.

Silicones

The silicones which can be used in the composition according to the present disclosure may be soluble or insoluble in the composition.

The silicones can, for example, comprise at least one polyorganosiloxane that is insoluble in the composition of the present disclosure and can be in a form chosen from oils, waxes, resins and gums.

The insoluble silicones are, in at least one embodiment, dispersed in the compositions in the form of particles having a number-average size ranging from 2 nanometers to 100 micrometers, such as from 20 nanometers to 20 micrometers (measured with a particle sizer).

The polyorganosiloxanes are defined in greater detail in the work by Walter NOLL "Chemistry and Technology of Silicones" (1968) Academic Press. They may be volatile or non-volatile.

Thus, the composition according to the present disclosure can comprise at least one volatile polyorganosiloxane, chosen from those having a boiling point of from 60° C. to 260° C., such as, for example:

(i) cyclic silicones having from 3 to 7 silicon atoms, such as 4 or 5. These cyclic silicones are, for example, the octamethylcyclotetrasiloxane sold, e.g., under the name "VOLATILE SILICONE 7207" by UNION CARBIDE or "SILBIONE 70045 V 2" by RHODIA, the decamethylcyclopentasiloxane sold under the name "VOLATILE SILICONE 7158" by UNION CARBIDE or "SILBIONE 70045 V 5" by RHODIA, and also mixtures thereof.

Mention may also be made of cyclocopolymers of the dimethylsiloxane/methylalkylsiloxane type, such as the "SILICONE VOLATILE FZ 3109" sold by the company UNION CARBIDE, which has the chemical structure:

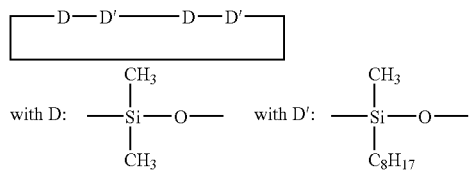

Mention may also be made of mixtures of cyclic silicones with silicon-derived organic compounds, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bisneopentane;

(ii) linear volatile silicones having 2 to 9 silicon atoms and possessing a viscosity of less than or equal to $5\times10^{-6}$ m$^2$/s at 25° C. These linear volatile silicones include, for example, the decamethyltetrasiloxane sold, e.g., under the name "SH 200" by the company TORAY SILICONE. Silicones which fall into this class are also described in the article published in Cosmetics and Toiletries, Vol. 91, January 76, p. 27-32—TODD & BYERS "Volatile Silicone fluids for cosmetics."

Similarly, the composition according to the present disclosure can comprise at least one non-volatile polyorganosiloxane, chosen from polyalkylsiloxanes, polyarylsiloxanes, polyalkylarylsiloxanes, silicone gums and resins, polyorganosiloxanes modified with organofunctional groups, polysiloxane(A)-polyoxyalkylene(B) linear block copolymers of (A-B)$_n$ type with n>3; grafted silicone polymers, with a non-silicone organic backbone, comprising an organic main chain formed from organic monomers containing no silicone, onto which is grafted, within said chain and also, optionally, at least one of its ends, at least one polysiloxane macromonomer; grafted silicone polymers, with a polysiloxane backbone grafted with non-silicone organic monomers, comprising a main chain of polysiloxane onto which is grafted, within said chain and also, optionally, at at least one of its ends, at least one organic macromonomer containing no silicone; and also mixtures thereof.

By way of examples of polyalkylsiloxanes, mention may, for example, be made of polydimethylsiloxanes with trimethylsilyl end groups having a viscosity of $5\times10^{-6}$ to 2.5 m$^2$/s at 25° C., such as $1\times10^{-5}$ to 1 m$^2$/s. The viscosity of the silicones is, for example, measured at 25° C. according to ASTM standard 445 Appendix C.

Among these polyalkylsiloxanes, mention may be made, in a non-limiting manner, of the following commercial products:

the SILBIONE oils of the 47 and 70 047 series or the MIRASIL oils sold by RHONE POULENC, such as, for example, the 70 047 V 500 000 oil;

the oils of the MIRASIL series sold by the company RHONE POULENC;

the oils of the 200 series from the company DOW CORNING, such as, more particularly, DC200 having a viscosity of 60 000 cSt;

the VISCASIL oils from GENERAL ELECTRIC and some oils of the SF series (SF 96, SF 18) from GENERAL ELECTRIC.

Mention may also be made of polydimethylsiloxanes with dimethylsilanol end groups (dimethiconol according to the CTFA name), such as the oils of the 48 series from the company RHONE POULENC.

In this class of polyalkylsiloxanes, mention may also be made of the products sold under the names "ABIL WAX 9800 and 9801" by the company GOLDSCHMIDT, which are poly(C$_1$-C$_{20}$)alkylsiloxanes.

The polyalkylarylsiloxanes can, in at least one embodiment, be chosen from linear and/or branched polydimethylmethylphenylsiloxanes and polydimethyldiphenyl-siloxanes having a viscosity of $1\times10^{-5}$ to $5\times10^{-2}$ m$^2$/s at 25° C.

Among these polyalkylarylsiloxanes, mention may, by way of example, be made of the products sold under the following names:

the SILBIONE oils of the 70 641 series from RHONE POULENC;

the oils of RHODORSIL 70 633 and 763 series from RHONE POULENC;

the DOW CORNING 556 COSMETIC GRADE FLUID oil from DOW CORNING;

the silicones of the PK series from BAYER, such as the product PK20;

the silicones of the PN and PH series from BAYER, such as the products PN1000 and PH1000;

some oils of the SF series from GENERAL ELECTRIC, such as SF 1023, SF 1154, SF 1250, and SF 1265.

The silicone gums which can be used in accordance with the present disclosure are, in at least one embodiment, polydiorganosiloxanes having high number-average molecular masses ranging from 200 000 to 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, or mixtures thereof.

Mention may be made, for example, of the following products:

polydimethylsiloxane,
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Silicone mixtures can also be used, such as:

the mixtures formed from a polydimethylsiloxane hydroxylated at the end of the chain (called dimethiconol according to the nomenclature of the CTFA dictionary) and from a cyclic polydimethylsiloxane (called cyclomethicone according to the nomenclature of the CTFA dictionary), such as the product Q2 1401 sold by the company DOW CORNING;

the mixtures formed from a polydimethylsiloxane gum with a cyclic silicone, such as the product SF 1214 Silicone Fluid from the company GENERAL ELECTRIC; this product is an SF 30 gum corresponding to a dimethicone, having a number-average molecular weight of 500 000 solubilized in the SF 1202 Silicone Fluid oil corresponding to decamethylcyclopentasiloxane;

the mixtures of two PDMSs having different viscosities, and, in at least one embodiment, of a PDMS gum and of a PDMS oil, such as the product SF 1236 from the company GENERAL ELECTRIC. The product SF 1236 is the mixture of an SE 30 gum defined above having a viscosity of 20 m$^2$/s and of an SF 96 oil having a viscosity of 5×10$^{-6}$ m$^2$/s. In another embodiment, this product contains 15% of SE 20 gum and 85% of an SF 96 oil.

The organopolysiloxane resins which can be used in accordance with the present disclosure are crosslinked siloxane systems containing the units: $R_2SiO_{2/2}$, $R_3SiO_{1/2}$, $RSiO_{3/2}$ and $SiO_{4/2}$ in which R is chosen from a hydrocarbon-based group having 1 to 16 carbon atoms and a phenyl group.

Among these products, those which are used according to at least one embodiment are those in which R is chosen from a $C_1$-$C_4$ lower alkyl radical, such as methyl, and a phenyl radical.

Among these resins, mention may be made of the product sold under the name "DOW CORNING 593" or those sold under the names "SILICONE FLUID SS 4230 and SS 4267" by the company GENERAL ELECTRIC and which are silicones with a dimethyl/trimethylsiloxane structure.

Mention may also be made of resins of the trimethylsiloxysilicate type sold in particular under the names X22-4914, X21-5034 and X21-5037 by the company SHIN-ETSU.

The organomodified silicones which can be used in accordance with the present disclosure are silicones as defined above and containing, in their structure, at least one organofunctional group attached by means of a hydrocarbon-based group.

Among the organomodified silicones, mention may be made of polyorgano-siloxanes containing:

polyethyleneoxy and/or polypropyleneoxy groups optionally comprising $C_6$-$C_{24}$ alkyl groups, such as the products called dimethicone-copolyol sold by the company DOW CORNING under the name DC 1248 or the SILWET® L 722, L 7500, L 77 and L 711 oils from the company UNION CARBIDE and the ($C_{12}$)alkyl methicone copolyol sold by the company DOW CORNING under the name Q2 5200;

substituted or unsubstituted amino groups, such as the products sold under the name GP 4 Silicone Fluid and GP 7100 by the company GENESEE or the products sold under the names Q2 8220 and DOW CORNING 929 or 939 by the company DOW CORNING. The substituted amino groups are, in at least one embodiment, $C_1$-$C_4$ aminoalkyl groups;

quaternary ammonium groups, such as the products sold under the names ABILQUAT 3272 and ABILQUAT 3474 by the company GOLDSCHMIDT;

thiol groups, such as the products sold under the names "GP 72 A" and "GP 71" from GENESEE;

alkoxylated groups, such as the product sold under the name "SILICONE COPOLYMER F-755" by SWS SILICONES and ABIL WAX® 2428, 2434 and 2440 by the company GOLDSCHMIDT;

hydroxyl groups, such as the polyorganosiloxanes with a hydroxyalkyl function, described in French patent application FR-A-85 16334;

acyloxyalkyl groups such as, for example, the polyorganosiloxanes described in U.S. Pat. No. 4,957,732;

anionic groups of the carboxylic acid type as, for example, in the products described in European Patent EP 186 507 from the company CHISSO CORPORATION, or of the alkylcarboxylic type such as those present in the product X-22-3701 E from the company SHIN-ETSU; 2-hydroxyalkyl sulphonate; 2-hydroxyalkyl thiosulphate, such as the products sold by the company GOLDSCHMIDT under the names "ABIL® S201" and "ABIL® S255";

hydroxyacylamino groups, such as the polyorganosiloxanes described in European Patent Application EP 342 834. Mention may, for example, be made of the product Q2-8413 from the company DOW CORNING.

The silicones used in at least one embodiment of the present disclosure are polydimethylsiloxanes such as polydimethylsiloxanes with trimethylsilyl end groups, or polydimethylsiloxanes with hydroxydimethylsilyl end groups, and aminated silicones.

The cosmetic composition according to the present disclosure comprises the at least one silicone in an amount of at least 0.1% by weight, relative to the total weight of the composition. In a further embodiment, the silicone is present in an amount of from 0.1 to 20% by weight, such as from 0.5 to 20% by weight, for instance, from 0.7 to 10% by weight or from 1 to 5% by weight relative to the total weight of the composition.

Mono- or Di-Esters of a Fatty Acid and of (Poly)Ethylene Glycol

The composition according to the present disclosure also comprises at least one mono- or diester of a fatty acid and of ethylene glycol or of polyethylene glycol.

The fatty acid(s) is (are), in at least one embodiment, $C_8$ to $C_{30}$, such as $C_{12}$ to $C_{24}$, fatty acids.

When the ester comprises a polyethylene glycol group, the latter comprises, in at least one embodiment, from 2 to 10 ethylene glycol units, such as from 2 to 5 ethylene glycol units.

In at least one embodiment, the ester is a monoester or a diester of a $C_{12}$ to $C_{24}$ fatty acid and of ethylene glycol. For example, the ester may be an ethylene glycol monostearate or distearate, or further still for example, may be ethylene glycol distearate.

The composition according to the present disclosure comprises, in at least one embodiment, at least 0.5% by weight of mono- or diester(s) of a fatty acid and of ethylene glycol or of polyethylene glycol, relative to the total weight of the composition, such as from 0.5 to 10% by weight, for example from 0.8 to 10% by weight, and in a still further embodiment, from 1 to 5% by weight of mono- or diester(s) of a fatty acid and of ethylene glycol or of polyethylene glycol, relative to the total weight of the composition.

Esters of $C_8$ to $C_{14}$ Fatty Acid and of Oxyethylenated Sorbitan

Finally, the composition which is the subject of the present disclosure comprises a specific nonionic surfactant comprising at least one ester of a $C_8$ to $C_{14}$ fatty acid and of an oxyethylenated sorbitan comprising from 2 to 10 oxyethylene units.

In at least one embodiment, the composition according to the present disclosure comprises at least one ester of a $C_{12}$ fatty acid and of an oxyethylenated sorbitan comprising from 2 to 10 oxyethylene units, such as 4 oxyethylene units.

In a further embodiment, the composition according to the present disclosure comprises oxyethylene sorbitan monolaurate with 4 OE. This compound is also known under the name polysorbate 21 and, inter alia, sold under the name TWEEN 21 by the company UNIQEMA.

The composition according to the present disclosure comprises the at least one ester of a $C_8$ to $C_{14}$ fatty acid and of oxyethylenated sorbitan comprising from 2 to 10 oxyethylene units in an amount of at least 0.5% by weight relative to the total weight of the composition. In a further embodiment, the at least one ester is present in an amount ranging from 0.5 to 10% by weight, such as from 2 to 9% by weight, or from 4 to 8% by weight, relative to the total weight of the composition.

The at least one ester of a $C_8$ to $C_{14}$ fatty acid and of an oxyethylenated sorbitan comprising from 2 to 10 oxyethylene units can be used alone, or as a mixture with at least one other oxyethylenated derivative of sorbitan. For example, in at least one embodiment, one may use at least one monoester of a $C_8$ to $C_{24}$ fatty acid and of an oxyethylenated sorbitan comprising from 15 to 50 oxyethylene units, for example, 20 oxyethylene units.

In a still further embodiment, said monoester of a $C_8$ to $C_{24}$ fatty acid and of an oxyethylenated sorbitan comprising 20 oxyethylene units is oxyethylene sorbitan mono-laurate with 20 OE.

The above-described monoester of a $C_8$ to $C_{24}$ fatty acid and of an oxythylenated sorbitan comprising from 15 to 50 oxyethylene units may be present in the composition according to the present disclosure in an amount of from 0.1 to 10%, such as from 0.5 to 5% by weight, relative to the total weight of the composition.

The compositions according to the present disclosure can, for example, be in the form of shower gels, shampoos, or compositions to be applied before or after a shampoo, the latter being in the form of a more or less thickened lotion, a gel or an emulsion.

Anionic Surfactants

The compositions of the present disclosure can also comprise at least one anionic surfactant.

The anionic surfactants which can be used in the compositions herein may be chosen, for example, from salts, e.g., alkali metal salts such as sodium salts, ammonium salts, amine salts, aminoalcohol salts or alkaline earth metal salts, for example magnesium salts, of the following types: alkyl sulphates, alkyl ether sulphates, alkylamido ether sulphates, alkylaryl polyether sulphates, monoglyceride sulphates, alkylsulphonates, alkylamidesulphonates, alkylarylsulphonates, α-Olefin sulphonates, paraffin sulphonates, alkylsulphosuccinates, alkyl ether sulphosuccinates, alkylamidesulphosuccinates, alkylsulphoacetates, acylsarcosinates and acylglutamates, the alkyl and acyl groups of all these compounds comprising from 6 to 24 carbon atoms and the aryl groups denoting, in at least one embodiment, phenyl or benzyl groups.

Use may also be made of $C_{6-24}$ alkyl monoesters of polyglycoside dicarboxylic acids, such as alkyl glucoside citrates, alkyl polyglycoside tartrates, and alkyl polyglycoside sulphosuccinates, alkylsulphosuccinamates, acylisethionates and N-acyltaurates, the alkyl or acyl group of all these compounds comprising from 12 to 20 carbon atoms.

Another group of anionic surfactants which can be used in the compositions of the present disclosure is that of acyl lactylates, the acyl group of which comprises from 8 to 20 carbon atoms.

In addition, mention may also be made of alkyl-D-galactosideuronic acids and salts thereof, and also polyoxyalkylenated ($C_{6-24}$ alkyl)ether carboxylic acids, polyoxyalkylenated ($C_{6-24}$ alkyl)($C_{6-24}$ aryl)ether carboxylic acids, polyoxyalkylenated ($C_{6-24}$ alkyl)amido ether carboxylic acids, and salts thereof, such as those comprising from 2 to 50 ethylene oxide units, and mixtures thereof.

In at least one embodiment, alkyl sulphates, alkyl ether sulphates and mixtures thereof are used, for example in the form of alkali metal or alkaline earth metal salts, ammonium salts, amine salts or aminoalcohol salts.

When present, the at least one anionic surfactant is present in an amount ranging from 0.5 to 50% by weight, such as from 4 to 20% by weight, relative to the total weight of the composition.

Nonionic Surfactants

The composition according to the present disclosure can also comprise, in addition to the at least one ester of a $C_8$ to $C_{14}$ fatty acid and of an oxyethylenated sorbitan comprising from 2 to 10 oxyethylene units, at least one additional nonionic surfactant different from the latter surfactant(s).

Examples of additional nonionic surfactants which can be used in the compositions of the present disclosure are described, for example, in "Handbook of Surfactants" by M. R. PORTER, publisher Blackie & Son (Glasgow and London), 1991, pp 116-178. The additional nonionic surfactants may be chosen, for example, from alcohols, alpha-diols, ($C_{1-20}$)alkylphenols, and polyethoxylated, polypropoxylated or polyglycerylated fatty acids having a fatty chain having, for example, from 8 to 18 carbon atoms, it being possible for the number of ethylene oxide or propylene oxide groups to range from 2 to 50 and it being possible for the number of glycerol groups to range from 2 to 30.

Mention may also be made of condensates of ethylene oxide and of propylene oxide with fatty alcohols; polyethoxylated fatty amides having, for example, from 2 to 30 ethylene oxide units, polyglycerylated fatty amides containing, on average, from 1 to 5 glycerol groups, such as from 1.5 to 4, ethoxylated fatty acid esters of sorbitan having from 2 to 30 ethylene oxide units, fatty acid esters of sucrose, fatty acid esters of polyethylene glycol, ($C_{6-24}$ alkyl)polyglycosides, N—($C_{6-24}$ alkyl)glucamine derivatives, and amine oxides such as ($C_{10-14}$ alkyl)amine oxides or N—($C_{10-14}$ acyl)aminopropylmorpholine oxides.

When present, the at least one additional nonionic surfactant is present in an amount ranging from 0.01 to 10% by weight, such as from 0.05 to 5% by weight relative to the total weight of the composition.

Amphoteric or Zwitterionic Surfactants

The compositions of the present disclosure can also comprise at least one amphoteric or zwitterionic surfactant.

The amphoteric or zwitterionic surfactants which can be used herein can, for example, be derivatives of secondary or tertiary aliphatic amines in which the aliphatic group is a linear or branched chain comprising from 8 to 22 carbon atoms and containing at least one anionic group such as, for example, a carboxylate, sulphonate, sulphate, phosphate or phosphonate group. Mention may also be made of ($C_{8-20}$) alkylbetaines, sulphobetaines, ($C_{8-20}$ alkyl)amido($C_{6-8}$ alkyl) betaines or ($C_{8-20}$ alkyl)amido($C_{6-8}$ alkyl)sulphobetaines.

Among the amine derivatives, mention may be made of the products sold under the name MIRANOL®, as described in U.S. Pat. No. 2,528,378 and U.S. Pat. No. 2,781,354 and classified in the CTFA dictionary, 3rd edition, 1982, under the names amphocarboxyglycinate and amphocarboxypropionate having the respective structures (I) and (II):

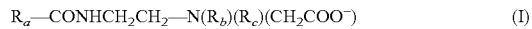

$$R_a\text{—CONHCH}_2\text{CH}_2\text{—N}(R_b)(R_c)(\text{CH}_2\text{COO}^-) \quad \text{(I)}$$

in which:
$R_a$ is an alkyl group derived from an acid $R_a$—COOH present in hydrolyzed coconut oil, or a heptyl, nonyl or undecyl group,
$R_b$ is a beta-hydroxyethyl group, and
$R_c$ is a carboxymethyl group; and

$$R_a'\text{—CONHCH}_2\text{CH}_2\text{—N(B)(B')} \quad \text{(II)}$$

in which:

B is —CH$_2$CH$_2$OX',

B' is —(CH$_2$)$_z$—Y', where z=1 or 2,

X' is chosen from —CH$_2$CH$_2$—COOH and hydrogen,

Y' is chosen from —COOH and —CH$_2$—CHOH—SO$_3$H,

R$_a$' is chosen from an alkyl group of an acid R$_a$'-COOH present in coconut oil or in hydrolyzed linseed oil, and an alkyl group, e.g., a C$_{1-7}$ alkyl group and its iso form, or an unsaturated C$_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylomphodipropionate, lauroamphodipropionic acid and cocoamphodipropionic acid.

By way of example, mention may be made of the cocoamphodiacetate sold by the company RHODIA under the trade name MIRANOL® C2M concentrate.

Among the amphoteric or zwitterionic surfactants mentioned above, (C$_{8-20}$ alkyl)betaines, (C$_{8-20}$ alkyl)amido(C$_{6-8}$ alkyl)betaines and mixtures thereof are used in at least one embodiment.

When present, the at least one amphoteric or zwitterionic surfactant is present in the composition in an amount ranging from 0.1 to 10% by weight, such as from 0.5 to 8% by weight, relative to the total weight of the composition.

The compositions according to the present disclosure have, in at least one embodiment, a total content of anionic, nonionic, amphoteric and zwitterionic surfactants ranging 4 to 50% by weight, such as from 4 to 20% by weight, relative to the total weight of the composition.

Cationic Surfactants

The composition according to the present disclosure can also comprise at least one cationic surfactant.

By way of examples of a cationic surfactant, non-limiting mention may be made of salts of primary, secondary or tertiary fatty amines, which are optionally polyoxyalkylenated; quaternary ammonium salts, such as tetraalkylammonium chlorides or bromides, alkylamidoalkyltrialkylammonium chlorides or bromides, trialkylbenzylammonium chlorides or bromides, trialkylhydroxyalkylammonium chlorides or bromides or alkylpyridinium chlorides or bromides; imidazoline derivatives; or amine oxides which are cationic in nature.

When the at least one cationic surfactant is present in the compositions disclosed herein, the amount thereof ranges, in at least one embodiment, from 0.01 to 10% by weight, such as from 0.05 to 5% by weight, and further, for example, from 0.3 to 3% by weight, relative to the total weight of the cosmetic composition.

In at least one embodiment, the composition disclosed herein comprises at least one anionic surfactant and at least one amphoteric or zwitterionic surfactant.

Cationic Polymers

The compositions according to the present disclosure can also comprise at least one cationic polymer.

The term "cationic polymer" is intended to mean any polymer containing cationic groups and/or groups which can be ionized to cationic groups.

The cationic polymers which can be used in accordance with the present disclosure can be chosen from all those already known per se as improving the cosmetic properties of hair treated with detergent compositions, for example, those described in European Patent Application EP-A-0 337 354 and in French Patent Applications FR-A-2 270 846, 2 383 660, 2 598 611, 2 470 596 and 2 519 863.

In at least one embodiment, the cationic polymers are chosen from those which contain units comprising primary, secondary, tertiary and/or quaternary amine groups which can either be part of the main polymer chain, or can be carried by a side substituent directly connected to said chain.

The cationic polymers used have a weight-average molecular mass of greater than $10^5$, such as greater than $10^6$, and further, for example, from $10^6$ to $10^8$.

In at least one embodiment, the cationic polymers may be polymers of the polyamine, polyaminoamide and quaternary polyammonium type. These are known products.

The polymers of the polyamine, polyamino amide and quaternary polyammonium type that can be used in the composition of the present disclosure are, for example, those described in French Patent Nos. 2 505 348 and 2 542 997. Among these polymers, mention may be made of:

(1) homopolymers or copolymers derived from acrylic or methacrylic esters or amides and containing at least one of the units having the following formulae:

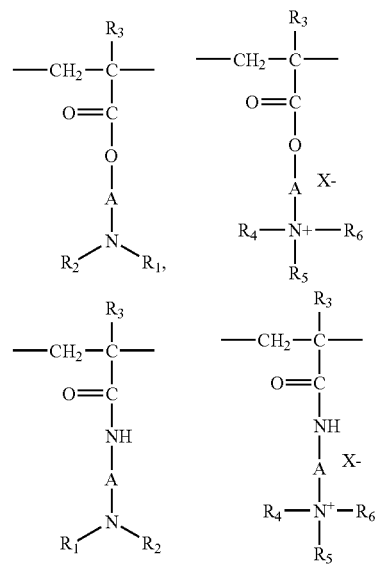

in which:

R$_1$ and R$_2$, which may be identical or different, are chosen from hydrogen and alkyl groups having from 1 to 6 carbon atoms, for example, from methyl and ethyl groups;

R$_3$, which may be identical or different, is chosen from hydrogen and a CH$_3$ group;

the symbols A, which may be identical or different, ar chosen from linear or branched alkyl groups comprising from 1 to 6 carbon atoms, such as from 2 or 3 carbon atoms, and from hydroxyalkyl groups comprising from 1 to 4 carbon atoms;

R$_4$, R$_5$ and R$_6$, which may be identical or different, are chosen from alkyl groups having from 1 to 18 carbon atoms and from benzyl groups, and, in at least one embodiment, alkyl groups having from 1 to 6 carbon atoms;

X is an anion derived from an inorganic or organic acid, such as a methosulphate anion or a halide, for instance chloride or bromide.

The copolymers of family (1) can also contain at least one unit derived from comonomers which can be chosen from the family of acrylamides, methacrylamides, diacetone acrylamides, acrylamides and methacrylamides substituted on the nitrogen atom with (C$_1$-C$_4$) lower alkyl groups, groups derived from acrylic or methacrylic acids or esters thereof, vinyllacatms such as vinylpyrrolidone or vinylcaprolactam, and vinyl esters.

Thus, among these copolymers of family (1), mention may be made of:

copolymers of acrylamide and of dimethylaminoethyl methacrylate quaternized with dimethyl sulphate or with a dimethyl halide, the copolymers of acrylamide and of methacryloyloxyethyltrimethyl-ammonium chloride described, for example, in European Patent Application EP-A-080 976, copolymers of acrylamide and of methacryloyloxyethyltrimethylammonium methosulphate, quaternized or nonquaternized vinylpyrrolidone/dialkylaminoalkyl acrylate or methacrylate copolymers. These polymers are described in detail in French Patent Nos. 2 077 143 and 2 393 573, dimethylaminoethyl methacrylate/vinylcaprolactam/vinylpyrrolidone terpolymers, vinylpyrrolidone/methacrylamidopropyldimethylamine copolymers, and quaternized vinylpyrrolidone/dimethylaminopropylmethacrylamide copolymers.

(2) The cellulose ether derivatives containing quaternary ammonium groups described in French Patent No. 1 492 597, such as the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble monomer of quaternary ammonium, and described, for example, U.S. Pat. No. 4,131,576, such as hydroxyalkylcelluloses, for instance hydroxymethyl-, hydroxyethyl- or hydroxypropylcelluloses grafted, in at least one embodiment, with a methacryloylethyltrimethylammonium, methacrylamido-propyltrimethylammonium or dimethyldiallylammonium salt.

The commercial products corresponding to this definition include, for example, the products sold under the name "Celquat® L 200" and "Celquat® H 100" by the company National Starch.

(4) The non-cellulose-based cationic polysaccharides described in U.S. Pat. Nos. 3,589,578 and 4,031,307, such as guar gums containing cationic trialkylammonium groups. Guar gums modified with a salt, for example 2,3-epoxypropyltrimethylammonium chloride, are, for example, used.

Such products are sold, for instance, under the trade names JAGUAR® C13S, JAGUAR® C15, JAGUAR® C17 or JAGUAR® C162 by the company MEYHALL.

(5) Polymers comprising piperazinyl units and divalent alkylene or hydroxyalkylene groups containing straight or branched chains, optionally interrupted with oxygen, sulphur or nitrogen atoms or with aromatic or heterocyclic rings, and also the oxidation and/or quaternization products of these polymers. Such polymers are described, for example, in French Patent Nos. 2 162 025 and 2 280 361.

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bisunsaturated derivative, a bishalohydrin, a bisazetidinium, a bishaloacyldiamine, a bis-alkyl halide or alternatively with an oligomer resulting from the reaction of a difunctional compound which is reactive with a bishalohydrin, a bisazetidinium, a bishaloacyldiamine, a bis-alkyl halide, an epihalohydrin, a diepoxide or a bisunsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, for example, in French Patent Nos. 2 252 840 et 2 368 508.

(7) The polyamino amide derivatives resulting from the condensation of polyalkylene polyamines with polycarboxylic acids, followed by alkylation with difunctional agents. Mention may, for example, be made of adipic acid/dialkylaminohydroxyalkyl-dialkylenetriamine polymers in which the alkyl group contains from 1 to 4 carbon atoms, such as a methyl, ethyl or propyl group, and the alkylene group contains from 1 to 4 carbon atoms, such as the ethylene group. Such polymers are described, for example, in French patent 1 583 363.

Among these derivatives, mention may be made, for example, of adipic acid/dimethylaminohydroxypropyldiethylenetriamine polymers.

(8) The polymers obtained by reaction of a polyalkylene polyamine containing two primary amine groups and at least one secondary amine group, with a dicarboxylic acid chosen from diglycolic acid and saturated aliphatic dicarboxylic acids having from 3 to 8 carbon atoms. The molar ratio of the polyalkylene polyamine to the dicarboxylic acid ranges from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

(9) Cyclopolymers of alkyldiallylamine or of dialkyldiallylammonium, such as homopolymers or copolymers containing, as main constituent of the chain, units corresponding to formula (Va) or (Vb):

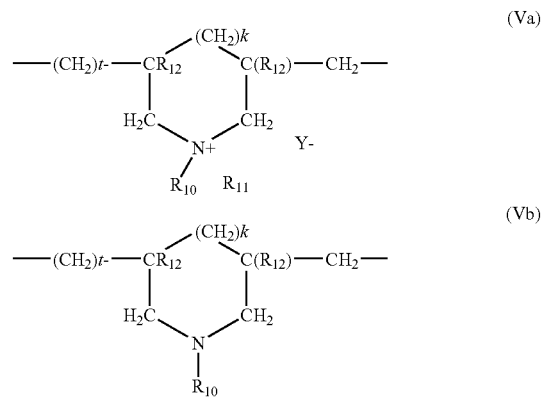

in which k and t are equal to 0 or 1, the sum k+t being equal to 1;

$R_{12}$ is chosen from a hydrogen atom and a methyl group;

$R_{10}$ and $R_{11}$, independently of one another, are chosen from alkyl groups having from 1 to 6 carbon atoms, hydroxyalkyl groups in which the alkyl group has, in at least one embodiment, 1 to 5 carbon atoms, lower ($C_1$-$C_4$)amidoalkyl groups, or alternatively $R_{10}$ and $R_{11}$ can form, together with the nitrogen atom to which they are attached, heterocyclic groups such as piperidinyl or morpholinyl;

$Y^-$ is an anion such as bromide, chloride, acetate, borate, citrate, tartrate, bisulphate, bisulphite, sulphate or phosphate.

These polymers are described, for example, in French Patent No. 2 080 759 and in its Certificate of Addition 2 190 406.

In at least one embodiment, $R_{10}$ and $R_{11}$, independently of one another, are chosen from alkyl groups having from 1 to 4 carbon atoms.

Among the polymers defined above, mention may, for example, be made of the dimethyldiallylammonium chloride homopolymer sold under the name "MERQUAT® 100" by the company CALGON (and its homologs of low weight-average molecular mass) and the copolymers of diallyldimethylammonium chloride and of acrylamide sold under the name "MERQUAT® 550".

(10) The quaternary diammonium polymers containing repeating units corresponding to formula (VI):

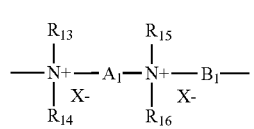
(VI)

in which:

$R_{13}$, $R_{14}$, $R_{15}$ and $R_{16}$, which may be identical or different, are chosen from aliphatic, alicyclic and arylaliphatic groups comprising from 1 to 20 carbon atoms or lower hydroxyalkyl aliphatic groups, alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ are chosen from linear or branched $C_1$-$C_6$ alkyl groups substituted with at least one group chosen from nitrile, ester, acyl and amide groups and from —CO—O—$R_{17}$-E or —CO—NH—$R_{17}$-E groups where $R_{17}$ is an alkylene group and E is a quaternary ammonium group;

$A_1$ and $B_1$ are chosen from polymethylene groups containing from 2 to 20 carbon atoms, which may be linear or branched, saturated or unsaturated, and which may contain, linked or intercalated in the main chain, at least one aromatic ring or at least one atom chosen from oxygen and sulphur atoms and from at least one group chosen from sulphoxide, sulphone, disulphide, amino, alkylamino, hydroxyl, quaternary ammonium, ureido, amide and ester groups, and $X^-$ is an anion derived from an inorganic or organic acid;

$A_1$, $R_{13}$ and $R_{15}$ can form, with the two nitrogen atoms to which they are attached, a piperazine ring; in addition, if $A_1$ is a linear or branched, saturated or unsaturated alkylene or hydroxyalkylene group, $B_1$ can also be a group:

—$(CH_2)_n$—CO-E'-OC—$(CH_2)_n$— in which E' is:

a) a glycol residue of formula —O—Z—O—, where Z is chosen from a linear or branched hydrocarbon-based group or a group corresponding to one of the following formulae:

—$(CH_2$—$CH_2$—O$)_x$—$CH_2$—$CH_2$—

—[$CH_2$—$CH(CH_3)$—O$]_y$—$CH_2$—$CH(CH_3)$— where x and y are independently an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula —NH—Y—NH—, where Y is a linear or branched hydrocarbon-based group, or alternatively the divalent group —$CH_2$—$CH_2$—S—S—$CH_2$—$CH_2$—;

d) a ureylene group of formula —NH—CO—NH—.

In at least one embodiment, $X^-$ is an anion such as chloride or bromide.

Polymers of this type are described, for example, in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may be made, in at least one embodiment, of polymers that comprise repeating units corresponding to the formula:

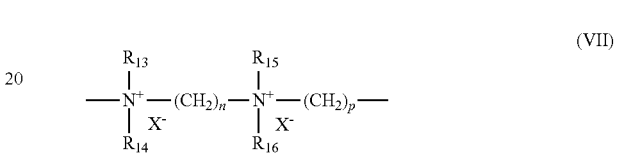
(VII)

in which $R_{13}$, $R_{14}$, $R_{15}$ and $R_{16}$, which may be identical or different, are chosen from alkyl or hydroxyalkyl groups having from 1 to 4 carbon atoms, n and p are integers ranging from 2 to 20, and $X^-$ is an anion derived from an inorganic or organic acid.

(11) Polyquaternary ammonium polymers comprising units of formula (VIII):

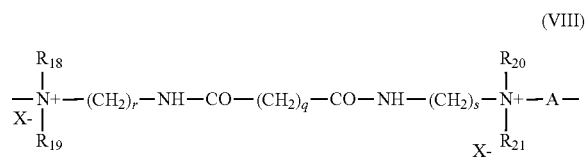
(VIII)

in which:

$R_{18}$, $R_{19}$, $R_{20}$ and $R_{21}$, which may be identical or different, are chosen from hydrogen and from methyl, ethyl, propyl, β-hydroxyethyl and β-hydroxypropyl groups and groups —$CH_2CH_2(OCH_2CH_2)_p$OH, where p is equal to 0 or to an integer ranging from 1 to 6, with the proviso that $R_{18}$, $R_{19}$, $R_{20}$ and $R_{21}$ do not simultaneously represent a hydrogen atom, r and s, which may be identical or different, are integers ranging from 1 to 6, q is equal to 0 or to an integer ranging from 1 to 34, $X^-$ is an anion such as a halide, A is a radical of a dihalide or is —$CH_2$—$CH_2$—O—$CH_2$—$CH_2$—.

Such compounds are described, for example, in European Patent Application EP-A-122 324.

(12) Quaternary polymers of vinylpyrrolidone and of vinylimidazole.

(13) Crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing olefinic unsaturation, for example, methylenebisacrylamide.

Other cationic polymers which can be used in the context of the disclosure are cationic proteins or cationic protein hydrolysates, polyalkyleneimines, such as polyethyleneimines, polymers containing vinylpyridine or vinylpyridinium units, condensates of polyamines and of epichlorohydrin, quaternary polyureylenes and chitin derivatives.

Among all the cationic polymers which can be used in the context of the present disclosure, use is made, in at least one embodiment, of cellulose ether derivatives containing quaternary ammonium groups, such as the products sold under the name "JR 400" by the company UNION CARBIDE CORPORATION, cationic cyclopolymers, such as the homopolymers or copolymers of dimethyldiallylammonium chloride sold under the names MERQUAT® 100, MERQUAT®550 and MERQUAT® S by the company CALGON, guar gums modified with a 2,3-epoxypropyltrimethylammonium salt, and quaternary polymers of vinylpyrrolidone and of vinylimidazole.

When the at least one cationic polymer is present, the composition according to the present disclosure comprises from 0.01 to 10% by weight of the at least one cationic polymer, such as from 0.1 to 5% by weight, and further, for example, from 0.1 to 2% by weight, relative to the total weight of the composition.

Anti-Dandruff Agents

The composition according to the present disclosure can also comprise at least one anti-dandruff agent. Anti-dandruff agents which can, for example, be used are compounds such as piroctone olamine, zinc pyrithione, salicylic acid or selenium disulphide, and mixtures thereof.

The composition then comprises from 0.001 to 10% by weight of anti-dandruff agent(s), such as from 0.1 to 5% by weight, and further, for example, from 0.2 to 2% by weight, relative to the total weight of the composition.

Aqueous Medium and pH

The aqueous medium comprises water or a mixture of water and of at least one cosmetically acceptable solvent chosen from $C_1$-$C_4$ lower alcohols, such as ethanol, isopropanol, tert-butanol or n-butanol; polyols such as glycerol, hexylene glycol, propylene glycol or polyethylene glycols, and mixtures thereof.

The pH of the compositions according to the disclosure is generally less than 8.5, such as from 4 to 7.

Additives

The composition according to the disclosure can also comprise at least one conventional additive well known in the art, such as anti-hairloss agents, oxidizing agents, ceramides and pseudoceramides, vitamins and provitamins, including panthenol, plant, animal, mineral or synthetic oils, waxes, sunscreens, colored or non-colored inorganic or organic pigments, dyes, sequestering agents, plasticizers, solubilizing agents, acidifying agents, basifying agents, inorganic or organic thickeners, antioxidants, hydroxy acids, fragrances and preserving agents.

Those skilled in the art will take care to choose the optional additives and the amounts thereof in such a way that they do not harm the properties of the compositions of the present disclosure.

These additives are present in the composition according to the present disclosure in an amount for each ranging from 0 to 20% by weight relative to the total weight of the composition.

Cosmetic Treatment

The composition according to the disclosure can be used, in at least one embodiment, as a composition for the cosmetic treatment or care of keratin materials.

As used herein, the term "keratin materials" is understood to mean the hair, the eyelashes, the eyebrows, the skin, the nails, the mucous membranes or the scalp, and, in at least one embodiment, refers to the hair.

In at least one embodiment, the composition according to the present disclosure can be used as a shampoo or a composition to be applied before or after a shampoo.

Another subject of the disclosure is a cosmetic treatment process which comprises the application to the hair of an effective amount of a cosmetic composition as described above.

According to one embodiment, such a process comprises applying to the hair an effective amount of the cosmetic composition, and in optionally rinsing it out after it has optionally been left on for a period of time.

When the composition is applied in the form of a lotion or a cream before or after shampooing, it is optionally left on the hair for ½ a minute to 5 minutes, and then optionally rinsed out with water.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contain certain errors necessarily resulting from the standard deviation found in their respective testing measurements.

The following examples are given by way of illustration of the present disclosure, and cannot limit the scope thereof.

EXAMPLES

In the following examples, all the amounts are indicated as percentage by weight of active material (AM) relative to the total weight of the composition, unless otherwise indicated.

Example 1

A first shampoo composition, in accordance with the present disclosure, was prepared from the ingredients indicated in the table below (in g of AM).

| | Composition 1 |
|---|---|
| sodium lauryl ether sulphate comprising 2.2 OE in aqueous solution at 70% AM (TEXAPON N702 from Cognis) | 15.3 |
| oxyethylene sorbitan monolaurate comprising 4 OE (TWEEN 21 from Uniqema) | 6 |
| cocoylamidopropylbetaine/glyceryl monolaurate in aqueous solution 25/75 by weight (TEGOBETAINE from Goldschmidt) | 1.6 |
| ethylene glycol distearate (Tegin BL 315 from Goldschmidt) | 2 |
| sodium N-cocoylamidoethyl, N-ethoxycarboxymethyl glycinate (MIRANOL C2M conc from Rhodia) | 0.8 |
| polydimethylsiloxane (PM 250 000) (MIRASIL DM 500 000 from Rhodia) | 2 |

-continued

| | Composition 1 |
|---|---|
| piroctone olamine (OCTOPIROX from Clariant) | 0.5 |
| sodium benzoate | 0.5 |
| fragrance | 0.5 |
| mixture of methyl, butyl, ethyl, propyl and isobutyl p-hydroxybenzoates (7/57/22/14) (NIPASTAT from Nipa) | 0.5 |
| powdered salicylic acid | 0.2 |
| carboxyvinyl polymer synthesized in an ethyl acetate/cyclohexane mixture (CARBOPOL 980 from Noveon) | 0.2 |
| methyl p-hydroxybenzoate | 0.03 |
| Water qs | 100% |

The shampoo composition detailed above was found to exhibit excellent tolerance with respect to the scalp. In particular, very few discomforting reactions were observed. In addition, this composition exhibited excellent ocular tolerance.

Finally, this composition exhibited good qualities for use, and also notable cosmetic softness, untangling and smoothing properties.

Examples 2 to 4

Three shampoo compositions, in accordance with the disclosure, were prepared from the ingredients indicated in the table below.

| | Compositions | | |
|---|---|---|---|
| | 2 | 3 | 4 |
| sodium lauryl ether sulphate (2.2 OE) in aqueous solution (TEXAPON N702 from Cognis) | 11.9 | 15.8 | 15.5 |
| cocoylamidopropylbetaine/glyceryl monolaurate in aqueous solution 25/75 (TEGOBETAINE from Goldschmidt) | 1.1 | 1.7 | — |
| oxyethylene sorbitan monolaurate comprising 4 OE (TWEEN 21 from Uniqema) | 6 | 6 | 6 |
| oxyethylene sorbitan monolaurate comprising 20 OE (TWEEN 20 from Uniqema) | — | — | 1 |
| ethylene glycol distearate (TEGIN BL 315 from Goldschmidt) | 2 | 2 | 2 |
| sodium N-cocoylamidoethyl, N-ethoxycarboxymethyl glycinate (MIRANOL C2M conc from Rhodia) | 0.8 | 0.8 | 3.1 |
| polydimethylsiloxane (MIRASIL DM 500 000 from Rhodia) | 1.5 | 2.7 | 2.7 |
| hexylene glycol (2-methyl-2,4-pentanediol) | 1 | — | — |
| coconut acid monoisopropanolamide (EMPILAN CIS from Huntsman) | 0.8 | — | — |
| sodium chloride | 0.5 | — | — |
| sodium benzoate | 0.5 | 0.5 | 0.5 |
| fragrance | 0.5 | 0.5 | 0.5 |
| mixture of methyl, butyl, ethyl, propyl, isobutyl p-hydroxybenzoates (7/57/22/14) (NIPASTAT from Nipa) | 0.5 | 0.5 | 0.5 |
| hydroxyethylcellulose quaternized with 2,3-epoxy-propyltrimethylammonium chloride (CELQUAT SC 240C from National Starch) | 0.4 | — | — |
| powdered salicylic acid | 0.2 | 0.2 | 0.2 |
| carboxyvinyl polymer synthesized in an ethyl acetate/cyclohexane mixture (CARBOPOL 980 from Noveon) | 0.2 | 0.2 | 0.15 |
| methyl p-hydroxybenzoate, sodium salt (NIPAGIN M sodium from Clariant) | 0.03 | 0.03 | 0.03 |
| guar hydroxypropyltrimethylammonium chloride (JAGUAR C13S from Rhodia) | — | 0.05 | 0.2 |
| Water qs | 100% | 100% | 100% |

The shampoo compositions detailed above were also found to exhibit excellent tolerance with respect to the scalp. In particular, very few discomforting reactions were observed. In addition, these compositions exhibited excellent ocular tolerance.

Finally, these compositions exhibited very good qualities for use, and also notable cosmetic softness, untangling and smoothing properties.

Example 5 to 7

Three shampoo compositions were prepared from the ingredients indicated in the table below. Composition 7 is in accordance with the disclosure, compositions 5 and 6 are presented by way of comparison.

| | Compositions | | |
|---|---|---|---|
| | 5 | 6 | 7 |
| sodium lauryl ether sulphate (2.2 OE) in aqueous solution (TEXAPON N702 from Cognis) | 11.7 | 11.7 | 11.7 |
| cocoylamidopropylbetaine/glyceryl monolaurate in aqueous solution 25/75 (TEGOBETAINE from Goldschmidt) | 1 | 1 | 1 |
| oxyethylene sorbitan monolaurate comprising 4 OE (TWEEN 21 from Uniqema) | — | — | 8 |
| oxyethylene sorbitan monolaurate comprising 20 OE (TWEEN 20 from Uniqema) | — | 8 | — |
| oxyethylene sorbitan monostearate comprising 4 OE (TWEEN 61 from Uniqema) | 8 | — | — |
| ethylene glycol distearate (TEGIN BL 315 from Goldschmidt) | 2 | 2 | 2 |
| sodium N-cocoylamidoethyl, N-ethoxycarboxymethyl glycinate (MIRANOL C2M conc from Rhodia) | 0.8 | 0.8 | 0.8 |
| polydimethylsiloxane (MIRASIL DM 500 000 from Rhodia) | 1 | 1 | 1 |
| coconut acid monoisopropanolamide (EMPILAN CIS from Huntsman) | 0.3 | 0.3 | 0.3 |
| sodium benzoate | 0.5 | 0.5 | 0.5 |
| fragrance | 0.5 | 0.5 | 0.5 |
| mixture of methyl, butyl, ethyl, propyl, isobutyl p-hydroxybenzoates (7/57/22/14) (NIPASTAT from Nipa) | 0.5 | 0.5 | 0.5 |
| hydroxyethylcellulose quaternized with 2,3-epoxypropyltrimethylammonium chloride (CELQUAT SC 240C from National Starch) | 0.4 | 0.4 | 0.4 |
| powdered salicylic acid | 0.2 | 0.2 | 0.2 |
| carboxyvinyl polymer synthesized in an ethyl acetate/cyclohexane mixture (CARBOPOL 980 from Noveon) | 0.2 | 0.2 | 0.2 |
| methyl p-hydroxybenzoate, sodium salt (NIPAGIN M sodium from Clariant) | 0.03 | 0.03 | 0.03 |
| Water qs | 100% | 100% | 100% |

Composition 7 according to the disclosure exhibited in particular, compared with the comparative compositions 5 and 6, advantages in terms of use and of viscosity.

First, the oxyethylene sorbitan monostearate comprising 4 OE that is used in comparative composition 5 had to be melted before it was incorporated into the shampoo, which made the preparation of the latter more difficult. Conversely, the oxyethylene sorbitan monolaurate comprising 4 EO that was used in composition 7 in accordance with the disclosure was liquid at ambient temperature. It could therefore be incorporated into the shampoo at ambient temperature, hence a substantial gain in terms of time and energy.

Second, the viscosities of comparative compositions 5 and 6 were not appropriate, compared with the usual consistency of shampoos.

Specifically, composition 6 had a flow time at 25° C. of 3 s CF 10, which corresponds to a viscosity that is too low, while composition 7 exhibited a flow time at 25° C. of 60 s CF 10, which corresponds to a viscosity more suitable for a shampoo.

Finally, composition 5 had a viscosity which is much too high.

Thus, composition 7 in accordance with the disclosure exhibited qualities for use that were superior to the comparative compositions: it was neither too thick nor too liquid, thus allowing better distribution of the product on the hair with a good foaming quality.

The invention claimed is:

1. A cosmetic composition for the care of keratin materials, comprising, in an aqueous medium:
    at least one silicone chosen from polydimethylsiloxanes having a viscosity at 25° C. ranging from $1\times10^{-5}$ to 1 $m^2/s$, present in an amount ranging from 0.1 to 10% by weight, relative to the total weight of the composition,
    at least one ethylene glycol distearate, present in an amount ranging from 1 to 5% by weight, relative to the total weight of the composition, and
    at least one ester of a $C_{12}$ fatty acid and of oxyethylenated sorbitan comprising from 2 to 10 oxyethylene (OE) units, present in an amount ranging from 2 to 9% by weight, relative to the total weight of the composition.

2. A cosmetic composition according to claim 1, wherein said composition comprises oxyethylenated sorbitan monolaurate comprising 4 OE.

3. A cosmetic composition according to claim 1, wherein said at least one silicone is present in an amount ranging from 0.7 to 10% by weight, relative to the total weight of the composition.

4. A cosmetic composition according to claim 1, said composition further comprising at least one additional monoester of a $C_8$ to $C_{24}$ fatty acid and of oxyethylenated sorbitan comprising 20 oxyethylene (OE) units.

5. A cosmetic composition according to claim 4, wherein said at least one additional monoester is a monoester of a $C_8$ to $C_{24}$ fatty acid and of oxyethylenated sorbitan comprising 20 oxyethylene units.

6. A cosmetic composition according to claim 4, wherein said at least one additional monester is oxyethylene sorbitan monolaurate comprising 20 OE.

7. A cosmetic composition according to claim 4, wherein said at least one additional monoester of a $C_8$ to $C_{24}$ fatty acid and of oxyethylenated sorbitan comprising from 15 to 50 oxyethylene units is present in an amount ranging from 0.1 to 10% by weight relative to the total weight of the composition.

8. A cosmetic composition according to claim 7, wherein said at least one additional monoester of a $C_8$ to $C_{24}$ fatty acid and of oxyethylenated sorbitan comprising from 15 to 50 oxyethylene units is present in an amount ranging from 0.5 to 5% by weight relative to the total weight of the composition.

9. A cosmetic composition according to claim 1, said composition further comprising at least one surfactant chosen from anionic, nonionic and amphoteric or zwitterionic surfactants.

10. A cosmetic composition according to claim 9, wherein said composition comprises at least one anionic surfactant and at least one amphoteric or zwitterionic surfactant.

11. A cosmetic composition according to claim 9, wherein said anionic surfactants are chosen from alkyl sulphates and alkyl ether sulphates, and mixtures thereof.

12. A cosmetic composition according to claim 9, wherein said at least one anionic surfactant is present in an amount ranging from 0.5 to 50% by weight relative to the total weight of the composition.

13. A cosmetic composition according to claim 12, wherein said at least one anionic surfactant is present in an amount ranging from 4 to 20% by weight, relative to the total weight of the composition.

14. A cosmetic composition according to claim 9, wherein the at least one amphoteric or zwitterionic surfactant is chosen form ($C_{8-20}$ alkyl)betaines and ($C_{8-20}$ alkyl)amino($C_{6-8}$ alkyl)betaines, and mixtures thereof.

15. A cosmetic composition according to claim 1, further comprising at least one cationic surfactant.

16. A cosmetic composition according to claim 1, further comprising at least one cationic polymer.

17. A cosmetic composition according to claim 16, wherein said at least one cationic polymer is present in an amount ranging from 0.01 to 10% by weight relative to the total weight of the composition.

18. A cosmetic composition according to claim 17, wherein said at least one cationic polymer is present in an amount ranging from 0.1 to 5% by weight, relative to the total weight of the composition.

19. A cosmetic composition according to claim 1, further comprising at least one anti-dandruff agent.

20. A cosmetic composition according to claim 19, wherein said at least one anti-dandruff agent is present in an amount ranging from 0.001 to 10% by weight, relative to the total weight of the composition.

21. A cosmetic composition according to claim 20, wherein said at least one anti-dandruff agent is present in an amount ranging from 0.1 to 5% by weight, relative to the total weight of the composition.

22. A cosmetic composition according to claim 1, wherein said at least one aqueous medium is chosen from water and from mixtures of water and of at least one cosmetically acceptable solvent.

23. A cosmetic composition according to claim 22, wherein the at least one solvent is chosen from $C_1$-$C_4$ lower alcohols and polyols.

24. A cosmetic composition according to claim 1, further comprising at least one additive chosen from anti-hairloss agents, oxidizing agents, ceramides, pseudoceramides, vitamins, provitamins, plant oil, animal oil, mineral oil, synthetic oil, waxes, sunscreens, colored or non-colored inorganic or organic pigments, dyes, sequestering agents, plasticizers, solubilizing agents, acidifying agents, basifying agents, inorganic or organic thickeners, antioxidants, hydroxyl acids, fragrances and preserving agents.

25. A method for washing the hair, said method comprising applying to the hair a shampoo composition comprising, in an aqueous medium:
    at least one silicone chosen from polydimethylsiloxanes having a viscosity at 25° C. ranging from $1\times10^{-5}$ to 1 $m^2/s$, present in an amount ranging from 0.1 to 10% by weight, relative to the total weight of the composition,
    at least one ethylene glycol distearate, present in an amount ranging from 1 to 5% by weight, relative to the total weight of the composition, and
    at least one ester of a $C_{12}$ fatty acid and of oxyethylenated sorbitan comprising from 2 to 10 oxyethylene (OE) units, present in an amount ranging from 2 to 9% by weight, relative to the total weight of the composition.

26. A method for treating the hair, said method comprising applying a shampoo composition to the hair and applying to the hair, either before or after the shampoo, a cosmetic composition comprising, in an aqueous medium:
    at least one silicone chosen from polydimethylsiloxanes having a viscosity at 25° C. ranging from $1\times10^{-5}$ to 1 m²/s, present in an amount ranging from 0.1 to 10% by weight, relative to the total weight of the composition, at least one ethylene glycol distearate, present in an amount ranging from 1 to 5% by weight, relative to the total weight of the composition, and at least one ester of a $C_{12}$ fatty acid and of oxyethylenated sorbitan comprising from 2 to 10 oxyethylene (OE) units, present in an amount ranging from 2 to 9% by weight, relative to the total weight of the composition.

27. A cosmetic treatment process, comprising applying to the hair an effective amount of a cosmetic composition comprising, in an aqueous medium:

- at least one silicone chosen from polydimethylsiloxanes having a viscosity at 25° C. ranging from $1 \times 10^{-5}$ to 1 m²/s, present in an amount ranging from 0.1 to 10% by weight, relative to the total weight of the composition,
- at least one ethylene glycol distearate, present in an amount ranging from 1 to 5% by weight, relative to the total weight of the composition, and
- at least one ester of a $C_{12}$ fatty acid and of oxyethylenated sorbitan comprising from 2 to 10 oxyethylene (OE) units, present in an amount ranging from 2 to 9% by weight, relative to the total weight of the composition.

* * * * *